(12) United States Patent
Gahman et al.

(10) Patent No.: US 9,226,831 B2
(45) Date of Patent: Jan. 5, 2016

(54) INTERVERTEBRAL IMPLANT (75) Inventors: Kevin Gahman, Douglassville, PA (US);
Marcin Niemiec, Bridgeport, PA (US);
David C. Paul, Phoenixville, PA (US);
Andrew Iott, Villanova, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 13/595,137

(22) Filed: Aug. 27, 2012

(65) Prior Publication Data
US 2014/0058513 A1 Feb. 27, 2014

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC .............. *A61F 2/442* (2013.01); *A61F 2/4465* (2013.01); *A61F 2/4611* (2013.01); *A61F 2002/2835* (2013.01); *A61F 2002/3008* (2013.01); *A61F 2002/30365* (2013.01); *A61F 2002/30367* (2013.01); *A61F 2002/30462* (2013.01); *A61F 2002/30466* (2013.01); *A61F 2002/30471* (2013.01); *A61F 2002/30472* (2013.01); *A61F 2002/30504* (2013.01); *A61F 2002/30505* (2013.01); *A61F 2002/30525* (2013.01); *A61F 2002/30538* (2013.01); *A61F 2002/30626* (2013.01); *A61F 2002/30629* (2013.01); *A61F 2002/30637* (2013.01); *A61F 2002/30779* (2013.01); *A61F 2002/30828* (2013.01); *A61F 2002/30843* (2013.01); *A61F 2002/4415* (2013.01); *A61F 2002/4475* (2013.01); *A61F 2002/4627* (2013.01); *A61F 2002/4629* (2013.01); *A61F 2310/00011* (2013.01); *A61F 2310/00023* (2013.01); *A61F 2310/00131* (2013.01)

(58) Field of Classification Search
CPC ........... A61F 2002/4415; A61F 2/4455; A61F 2/4465; A61F 2002/4475; A61F 2002/448; A61F 2002/4485
USPC .......................................... 623/17.11–17.16
See application file for complete search history.

(56) References Cited

U.S. PATENT DOCUMENTS

| | | | |
|---|---|---|---|
| 64,757 A * | 5/1867 | Garlinghouse | ............... 403/121 |
| 7,682,400 B2 * | 3/2010 | Zwirkoski | .................. 623/23.48 |
| 2003/0050693 A1 * | 3/2003 | Quijano et al. | .............. 623/2.11 |
| 2008/0133012 A1 * | 6/2008 | McGuckin | ................. 623/17.12 |
| 2008/0221694 A1 | 9/2008 | Warnick | |
| 2008/0249628 A1 * | 10/2008 | Altarac et al. | ............. 623/17.16 |
| 2009/0030423 A1 * | 1/2009 | Puno | .............................. 606/99 |

(Continued)

*Primary Examiner* — Eduardo C Robert
*Assistant Examiner* — Julianna N Harvey (57) ABSTRACT

An intervertebral spacer for therapeutic treatment of a patient includes at least one link sized and dimensioned to fit within an intervertebral space in the patient, and is configured to maintain a separation of two adjacent vertebrae for a period of time. A rigid guiding object, which may be a tool or a successive link, is insertable into the patient, to guide other links into the patient using an MIS approach. A pivot is connected between successive links, or between a guide tool and a link, configured to limit a relative range of angular orientation between the link and the guiding tool, or successive links. Multiple links are so joined to form a chain pushable by the last link, and pullable by the first link, to form a chain which may be formed into a curved configuration corresponding to the patient's intervertebral space.

20 Claims, 4 Drawing Sheets

(56) References Cited

U.S. PATENT DOCUMENTS

| | | |
|---|---|---|
| 2010/0094422 A1 | 4/2010 | Hansell |
| 2010/0145386 A1* | 6/2010 | Greenhalgh et al. .......... 606/246 |
| 2011/0093072 A1* | 4/2011 | Siegal ........................ 623/11.11 |
| 2011/0276142 A1 | 11/2011 | Niemiec |
| 2011/0282459 A1 | 11/2011 | McClellan |
| 2012/0010717 A1 | 1/2012 | Spann |

* cited by examiner

INTERVERTEBRAL IMPLANT

FIELD OF THE INVENTION

The invention relates to intervertebral spacing, and more particularly to an intervertebral spacer that may be inserted and guided into place through a cannula.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae. Preparation of the intervertebral disc space includes maneuvering a cutting tool within a small space. The foregoing and other diseases may benefit from the removal or shaping of body tissue through a minimal incision, for example in a laparoscopic procedure, where the tool must be sufficiently small to pass through a small opening in the body. Once access to the intervertebral space is attained a spacer is inserted into the intervertebral space.

SUMMARY OF THE INVENTION

In accordance with the disclosure, an intervertebral spacer for therapeutic treatment of a patient, comprises at least one link sized and dimensioned to fit within an intervertebral space in the patient and configured to maintain a separation of two adjacent vertebrae for a period of time; at least one rigid guiding object insertable into the patient, the at least one rigid guiding object and the at least one link sized to be insertable into the patient using an MIS approach; and at least one multiaxial pivot connected between an end of one of the at least one link and an end of one of the at least one rigid guiding object, the at least one pivot configured to limit a maximum relative range of angular orientation of the one of the at least one link and the one of the at least one rigid guiding object, the at least one pivot configured to transfer an insertion force from the at least one rigid guiding object to the at least one link, to advance the at least one link into the intervertebral space.

In an embodiment of the intervertebral spacer, there is further included an elongated guide member having a proximal end extendable outside the body and a distal end extendable into the body connectable to the at least one pivot; and at least one of the at least one pivot having a mechanical connector releaseably mateable with the mechanical connector of the distal end of the elongated guide member, the at least one of the at least one pivot rotatable within a chamber in at least one of the at least one link.

In another embodiment, the at least one of the at least one pivot includes a radiused nut supporting the mechanical connector of the at least one of the at least one pivot; a pin pivotally supportable within at least one of the at least one links; and a chamber within the pin, the chamber having an internal surface mateable with the radius of the radiused nut, the radiused nut rotatable within the chamber; the mechanical connector of the elongated guide member connectable to the mating mechanical connector supported by the nut when the nut is within the chamber, and the pin is pivotally supported within the one of the at least one link. In yet another embodiment, the spacer further includes a tapered edge formed along at least one end of at least one of the at least one link.

In accordance with another embodiment of the disclosure, an intervertebral spacer for therapeutic treatment of a patient, comprises a plurality of flexibly connected links sized and dimensioned to fit within an intervertebral space in the patient and configured to maintain a separation of two adjacent vertebrae for a period of time, the links insertable into the patient through a tube using a reduced size MIS incision; and a plurality of pivots each forming the flexible connection between adjacent ones of the plurality of links, the plurality of pivots configured to limit a relative range of motion of adjacent links relative to each other, the plurality of pivots cooperative to form the plurality of links into a radiused configuration corresponding to cortical bone within an intervertebral space of the patient.

In an embodiment thereof, the plurality of pivots are configured to form a chain of the plurality of links having a leading link and a trailing link, the trailing link pushable to advance the chain into the vertebral space, the leading link pullable to guide the chain into a curved configuration corresponding to the patient's intervertebral space.

In another embodiment, the plurality of links include at least three links connected one to another by one of the plurality of pivots, the at least three links insertable into the body in a first relative substantially aligned orientation relative to each other, and formable into a curved alignment in the intervertebral space, a plurality of links positionable at least in part over cortical bone in the intervertebral space.

Other embodiments include an elongated guiding member configured to pass into the body and push the plurality of links into the intervertebral space; an elongated guiding member configured to extend from outside of the patient's body into the patient's body, and to push the plurality of links within the intervertebral space.

In one embodiment, the plurality of pivots consisting of a linkage selected from the group consisting of: gears, flexible fibers, an elastomeric link, a plate and pins, and a pin. In another embodiment, the plurality of pivots include a flexible connector extending between and connected to adjacent ones of the plurality of links, and a latch mechanism operative to maintain an angular displacement between the adjacent ones of the plurality of links when the adjacent ones of the plurality of links are pivoted to a predetermined angle relative to each other. In a variation thereof, the latch mechanism selected from the group consisting of hook and catch, hooks and loops, magnetic elements, and mechanical latch.

In yet further embodiments, the spacer includes a stop projection adjacent at least one of the plurality of pivots, the stop configured to limit an extent of angular displacement between adjacent ones of the plurality of links; at least one of the plurality of links including one or more apertures through which bone of the patient may grow; at least one of the plurality of links including a therapeutic substance operative to promote at least one of healing, anti-microbial growth, and bone growth; at least two of the plurality of links have a substantially different shape; and the spacer includes an aperture formed in at least one end of at least one of the plurality of links, the aperture sized to admit passage of a flexible line passable through the aperture when the link is within the intervertebral space to extend outside of the patient, the link configured to rotate within the intervertebral space when a force is exerted upon the line.

In accordance with various methods of the disclosure, any of the spacer embodiments may be inserted into the body through a tube extending from outside of the patient's body into the patient's body. Further, a method may include passing a flexible line through an aperture formed in a leading end of at least one of the plurality of links, the leading end defined as the end first advanced into the intervertebral space, the line passing from outside of the patient's body, through the aperture, and back outside the patient's body, the line having sufficient strength to guide the leading by exerting a force upon the leading end when the plurality of links is advanced into the intervertebral space.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Figures 1, 2, 2A, 3:
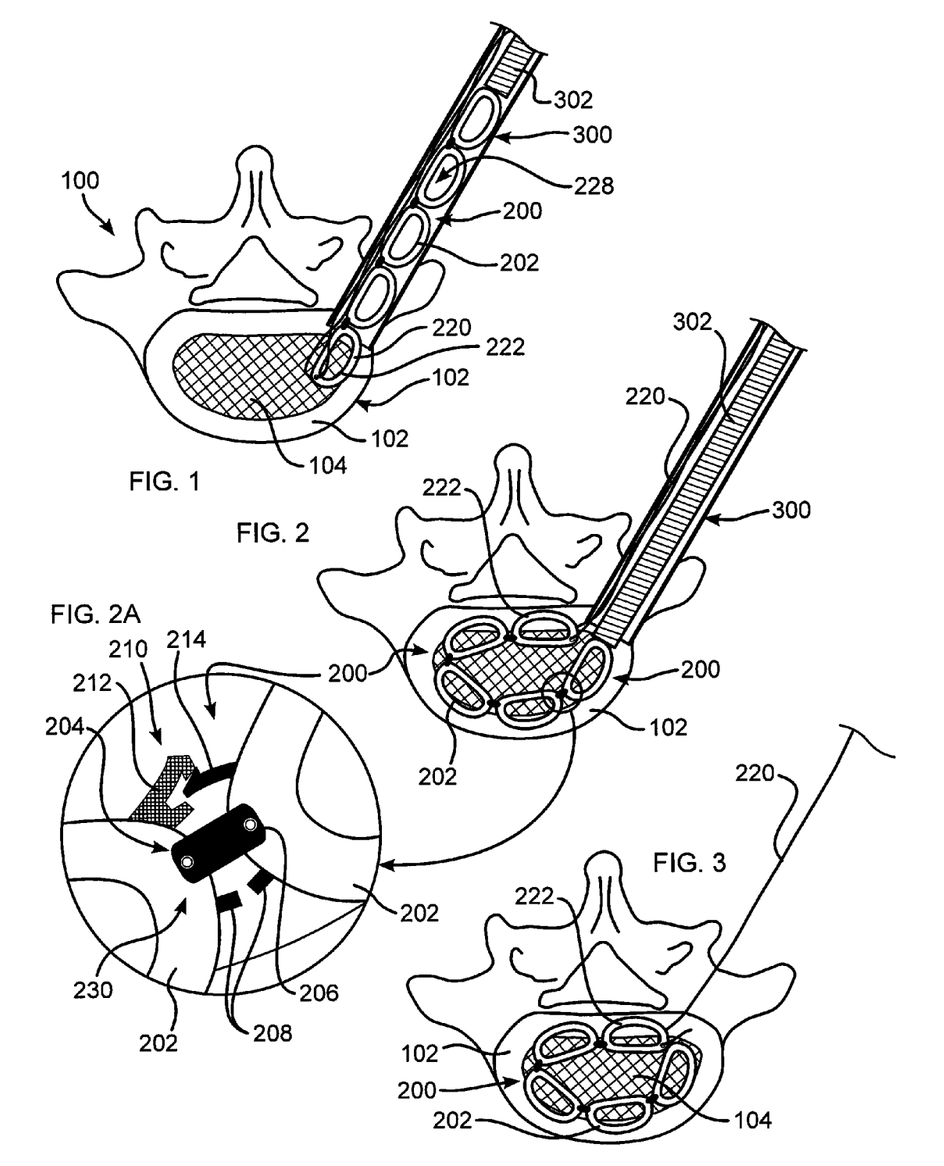
FIG. 1 depicts a cross-sectional view of a spacer of the disclosure being inserted into an intervertebral space.
FIG. 2 depicts the spacer of FIG. 1 substantially in position within the intervertebral space.
FIG. 2A depicts an enlarged view of a portion of the spacer of FIG. 2, depicting a latching mechanism associated with a spacer of the disclosure.
FIG. 3 depicts spacer of FIG. 1 within the intervertebral space, and a guiding line being removed from the body.

With reference to FIG. 1, an intervertebral cage or spacer 200 that overlies a substantial portion of a vertebral body 102 of a vertebra 100 of a patient, and is admitted into the body and the intervertebral space through a minimally invasive incision and method. More particularly, spacer 200 forms a narrow elongated profile comprising a series of links 202. As may be seen in in FIG. 1, links 202 may be linearly aligned in order to pass through an incision that may have the same, or smaller width, than a width of the widest link 202.

In one embodiment of the disclosure, a tube, guide channel, or cannula 300 is passed through the incision to a position proximate an intervertebral space into which spacer 200 is to be implanted. Cannula 300 is sized to admit a linear formation of links 202, and may stretch skin and other body tissue (not shown) of a passageway through the body that is narrower than cannula 300 or elongated spacer 200. In alternative, a retractor or retractor system is used to form a passage to the intervertebral location, through which spacer 200 may be passed.

Spacer 200 may be inserted using a Lumbar Interbody Fusion or a TLIF (Transforaminal Lumbar Interbody Fusion) approach. Once spacer 200 is inserted, it is formed into a loop to overlie a large portion of the contact area between adjacent vertebrae. More particularly, there is a high correlation between bone quality and rate of interbody cage subsidence. Accordingly, to increase a probability of long term stabilization, particularly with poor bone quality, for example due to disease, spacer 200 is formed to assume a profile having a large surface area once therapeutically positioned, but is passable into the body while formed into a small or narrow profile. The narrow profile enables a MIS (minimally invasive surgical) approach, which minimizes disruption to untargeted anatomy. In one embodiment, spacer 200 overlies both cortical bone 104 and cancellous bone 106 of the vertebral body 102.

With further reference to FIGS. 1-3, links 202 our pivotally joined to each other so that successive links may bend, at least, in one common direction. In this manner, spacer 200 may convert from an elongate chain during insertion, to a circular chain when disposed between vertebrae. A pivoting joint 230 is illustrated in FIG. 2A, in which a plate 204 is shown having two link pins 206 each connecting plate 204 to a link 202. It should be understood, however, that plate 204 may be fused to one link 202, or may simply be formed of extending material of one link 202 connected by a single pin, and pivot only in connection with the adjacent link. Alternatively, link 202 may be formed of a flexible material, such as an elastomer, or may be formed as flexible fibers, and may be securely fastened to each adjacent link 202. Accordingly, a connection is formed between adjacent links 202, using any known means, which enables an angular orientation or range of motion between adjacent links 202 to be changed, at least in one direction, so that links 202 of a chain may be mutually angled from a substantially linear alignment into a looped, rounded, oval, oblong, or circular shape. Advantageously, the connection formed between links is multiaxial or polyaxial, allowing angular relative displacement of successive links upon many planes.

Spacer 200 advantageously shapes to conform to the anatomy of the patient, for example matching the concavity of vertebral body endplates. Additionally, tapering edge 250 advantageously distracts the disc space as a link is inserted.

FIG. 2A additionally illustrates that links 202 may be formed to abut if angled in a direction opposite to an intended direction, for example to form a loop extending away from a center of the vertebral body 102. Links 202 may be shaped to abut, or may be provided a stopping projection 208, for example pins or projections which preclude or prevent substantial angular relative movement of adjacent links in an undersired direction. Additionally illustrated is a latching mechanism 210 which serves to secure adjacent links 202 in a desired relative orientation, thereby reducing a likelihood of undesired migration of spacer 200 within the body. In the embodiment illustrated, a resilient catch 212 bends to allow insertion of a mating hook 214, the engagement of catch 212 and hook 214 preventing substantial reorientation of adjacent links 202. Other mechanisms may be used to secure successive links in a desired final orientation, including for example hook and loop fasteners, magnetic elements, and other forms of mechanical latches. Alternatively, a latch may be omitted if migration is not anticipated or of concern.

Initially, spacer 200 may be urged into the body by pushing on one or more of links 202. It may further be advantageous, particularly as spacer 200 becomes inaccessible for direct manipulation, to use a pushing tool or pushing member 302, such as for example a rod, hemostat, or other tool or rigid object, to urge and position spacer 200 into and within the body. In the embodiment illustrated in FIGS. 1-2, pushing tool or member 302 is extended within cannula 300 to urge and guide spacer 200 along an inner bore of cannula 300 and into the intervertebral space.

As may further be seen in FIGS. 1-3, a flexible guide line 220 is advantageously connected to one or more links 202, in order to control a positioning of links 202 within the body. In the example shown in FIGS. 1-3, line 220 is connected to first link 222, which is advantageously one of the first links to enter the body, and is used to pull first link 222 towards a final desired position of first link 222. Consequently, as additional links are pushed into the intervertebral space, they will be forced to bend relative to each other, and will therefore tend to form a loop which spreads about the surface of a vertebral body 102, advantageously overlying both cortical and cancellous bone 104, 106 of vertebral body 102. Line 220 may be fabricated using any material of suitable strength and thickness, including suture material, or metallic wire, for example.

Once links 202 are in a therapeutically advantageous position, cannula 300 may be removed from the body. Additionally, line 220 may be removed from the body before or after cannula 300 is removed from the body. To facilitate removal, a free end of line 220 may be passed through an aperture 224 in link 222 and the free end then extended outside the body where it may be controlled. To release line 220, the free end is released and line 220 may be removed from the body. Another method of controlling line 220 is described with respect to FIG. 5, herein.

Figures 4, 5, 6:
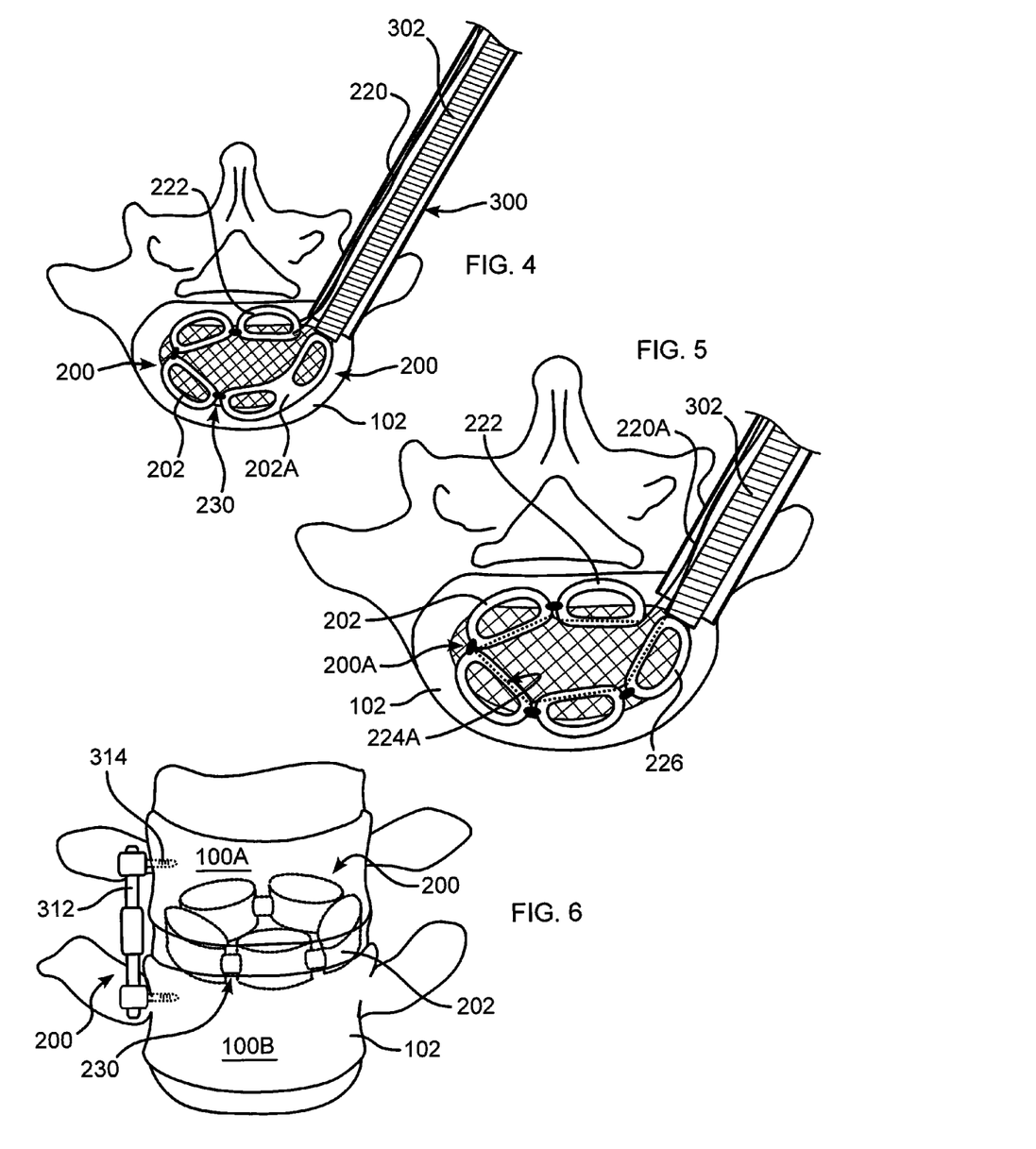
FIG. 4 depicts an alternative spacer of the disclosure, illustrating variable sized and or shaped links.
FIG. 5 depicts an alternative guiding line configuration of the disclosure.
FIG. 6 depicts a perspective view of a spacer of the disclosure implanted between vertebrae.

Referring now to FIG. 4, a spacer 200A includes a link 202A that is dissimilarly shaped with respect to remaining links 202. In the embodiment shown, link 202A is elongated with respect to links 202, and facilitates final placement of spacer 200. In accordance with the disclosure, a link 202A having a particular shape, for example longer, wider, taller, or having a different curvature, may be positioned proximate an area of the body which would benefit from different support than might be provided by a commonly shaped link. For example, link 202A may be sized and dimensioned to fit an area of damaged tissue. Alternatively, link 202A may be dissimilarly shaped to facilitate guiding links 202 into a particular final configuration, for example by having a fixed curvature, such as is shown in FIG. 4.

An alternative line 220A is illustrated in FIG. 5, in which line 220A is passed through or otherwise connected with a plurality of links, to facilitate causing links 202 to "double back", or curl into a curved shape corresponding to the anatomy of the patient. More particularly, an aperture 224A is provided within more than one link 202, through which line 220A is passed. In the embodiment shown, aperture 224A passes through a side of link 202A, but it should be understood that line 220A may be threaded through one or more loops or relatively shorter holes formed in link 202A. In this manner, tension on one or both ends of line 224A operates to cause spacer 200A to curl upon itself to conform to patient anatomy. Advantageously, one free end of line 220A is held stationary, while the other is pulled, to urge the formation of a circular configuration of links 202 of spacer 200A.

In this embodiment, pushing member 302 may exert an insertion force against last link 226, and a force applied to line 220A influences all links through which it is passed, to guide spacer 200A into a desired configuration, for example a curved configuration conforming to the patients anatomy in the intervertebral space. Line 220A may be removed from the body as described for line 220, in particular, either of two loose ends passed outside the body may be pulled to disengage line 220A from spacer 200A. It should be understood that it is advantageous for spacer 200/200A to follow a predetermined path within the patient, to avoid impacting a non-targeted area of the patient, particularly including nerve tissue.

FIG. 6 illustrates spacer 200/200A (herein spacer 200) positioned between two adjacent vertebrae. A spinal stabilizer 310 is illustrated, cooperative with spacer 200, to provide further stabilization to the spine. In one embodiment, stabilizer 310 is configured to limit a superior/inferior separation of vertebrae 102A, 102B, and or to limit a lateral displacement of vertebra 100A with respect to vertebra 100B. While spacer 200 operates to maintain a minimum separation of vertebrae 102A, 102B, stabilizer 310 may also contribute to maintaining this minimum separation, particularly where bone of the joint is weakened. While one stabilizer 310 is shown, any number of stabilizing elements may be used in cooperation with spacer 200, for example plates, adhesive, screws, sutures, graft material, scaffolds, or any other known or hereinafter developed stabilizing device. In the example shown, stabilizer 310 is a rigid or flexible rod 312 connected to a vertebra 102 at each end, in this example with polyaxial pedicle screws 314.

With reference to FIGS. 7-15, in one embodiment of the disclosure, a shaped link is passed into the body as described with respect to the previous embodiments. In this embodiment, however, link 202B is elongated with respect to the examples illustrated in FIGS. 1-6, and may support adjacent vertebrae alone, or in combination with other links 202, as described herein. Further in accordance with this embodiment, pushing member 302 exerts a force against a trailing end 228 of link 202B, and line 220 is passed through a leading end 232. In this manner, a predetermined final orientation of link 202B may be achieved by adjusting the relative force applied by pushing member 302 (in the embodiment illustrated, lever 238, described below) and line 220. To facilitate insertion through or between body tissue, leading end 232 may be provided with a tapering edge 250, which reduces an insertion force and or reduces trauma to body tissue while gradually separating body tissue.

Figures 7, 8, 9:
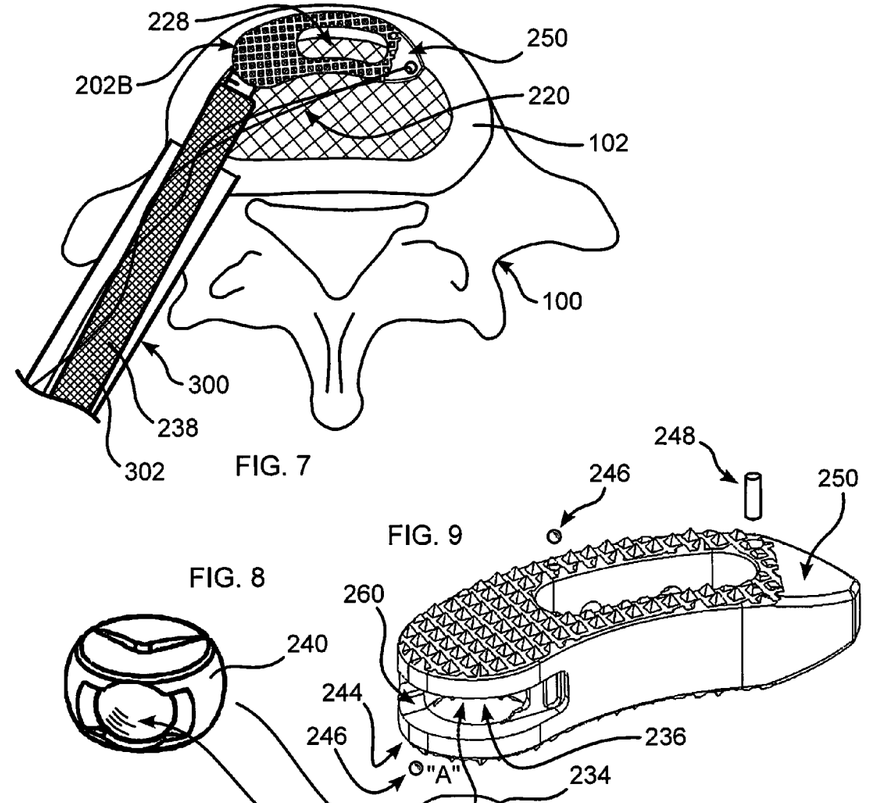
FIG. 7 depicts an alternative embodiment of a link and guiding tool of the disclosure.
FIG. 8 depicts an exploded view of the link and tool of FIG. 7.
FIG. 9 depicts a bottom view of the link of FIG. 7.
Figures 10, 11:
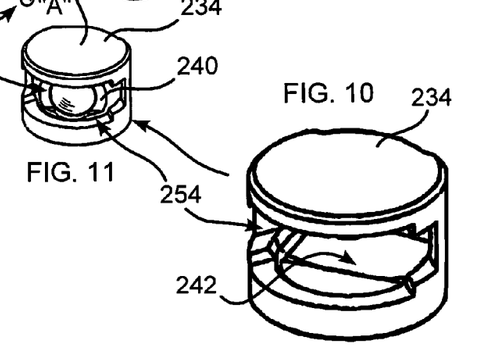
FIG. 10 depicts a side view of the link of FIG. 7.
FIG. 11 depicts a top view of the link of FIG. 7.
Figure 12:
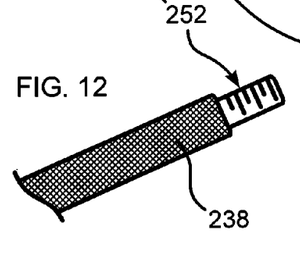
FIG. 12 depicts the lever.
Figures 13, 14, 15:
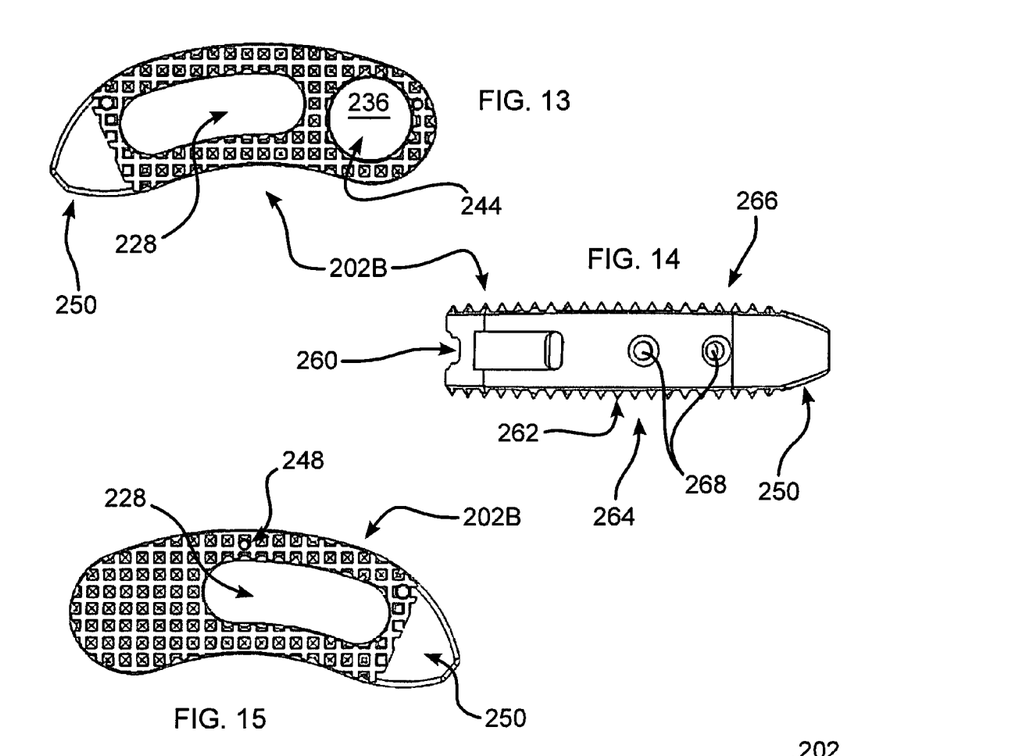
FIGS. 13, 14, and 15 depict a bottom view, a side view and a top view of the intervertebral implant, respectively.

FIG. 9 illustrates an exploded view of an alternative configuration of link 202B, although it should be understood that the elements described as follows may be associated with a link 202, 222, 226 of spacer 200 in any embodiment described herein. More particularly, a pivot pin 234 is rotatably retained within a mating chamber 236 formed within a link 202 of the disclosure, and in this example, link 202B. In one embodiment, a chamber portal 244 is formed within at least one side of link 202B sized to admit passage of pin 234, in this embodiment, along the direction indicated by arrow "A". An interference fit may be provided between portal 244 and pin 234, to prevent an unintended release of pin 234 from chamber 236 through portal 244, or a retaining member may be provided to maintain pin 234 within chamber 236, for example a threaded collar or ratchet (not shown).

Pivot pin 234 in one embodiment is mateable with a pushing member 302 having the form of a positioning lever 238, for example using a mating threaded, interlocking, or other releasable mechanical connection 252, so that link 202B may be inserted into the body using lever 238, and manipulated, for example rotated or moved laterally, in addition to pushing and pulling, into a predetermined desired position using lever 238 once link 202B has been inserted between vertebrae, for example using an impaction force imparted by lever 238. Link 202B, or a series of links if interconnected as described herein, may be pushed into the intervertebral space using lever 238, which may be extended from inside the body to a position outside the body.

In the embodiment shown, to enable a greater range of motion of lever 238 with respect to link 202B, a spherical or radiused nut 240 is inserted within a mating radiused chamber 242 formed within pivot pin 234. Radiused nut 240 may be retained within radiused chamber 242 using an interference fit or a retainer, as described for retention of pin 234 within chamber 236. In this embodiment, a slot 254 is formed within pin 234, to allow sliding passage of a manipulating element, for example lever 238, wherein lever 238 is releasably engageable with radiused nut 240, for example using a threaded, interlocked, or other mechanical connection. In this manner lever 238 may be moved through a range of vertical and horizontal angles while manipulating link 202B. More particularly, slot 254 is advantageously substantially wider and taller than a maximum dimension of lever 238 at a location where lever 238 passes through slot 254. A corresponding sized slot 260 within link 202B is provided, sized and dimensioned to admit passage and movement of lever 238 into chamber 236, advantageously allowing movement of lever 238 throughout a range permitted by slot 254. In one embodiment, the implant is constrained to a rotation of 75 degrees along an A/P or lateral direction during insertion, although a smaller or wider range of rotation may be permitted, for example within a range of 35 to 145 degrees. It should be understood that slot 254 and 260, or a combination of slots 254, 260, cooperate with radiused nut 240 to enable a given range of motion in a superior/inferior direction as well, although a smaller angular range is advantageous. Thus, the connection formed between lever 238 and link 202B is polyaxial or multiaxial, whereby a spacer 200, or implant of the disclosure may be inserted into the disc space in an off-axis, non-linear, or otherwise less than ideal anatomic conditions, at any of a wide variety of relative angles between lever 238 and link 202B, including upwards/downwards, and sideways relative angles upon many planes.

Further, radiused nut 240, which securely engages an end of lever 238, conformingly engages radiused chamber 242, to efficiently transfer forces applied to lever 238 to link 202B, throughout an entire range of motion of lever 238 within slot 254. Radiused nut 240 facilitates attachment of an insertion tool, such as lever 238, by reducing the potential for internal thread deformation by enabling movement, within predetermined limits, of link 202/202B with respect to lever 238. Additionally, radiused nut 240 is advantageously limited in its movement, for example by bearings 246 or a cammed mating engagement (not shown), so that a mechanical connection 252 between radiused nut 240 and lever 238 is always readily possible.

Link 202B may further be provided with bearings 246 operative to promote smooth movement of pin 234 within chamber 236. In one embodiment, bearings 246 are configured and operative to limit a range of motion of pin 234, for example by traveling within cooperating slots (not shown) formed in mating surfaces of pin 234 and chamber 236. It should be understood that one or more additional links 202 as described herein may be connected to a leading end of link 202B using any of the linkages described herein, including a pivoting linkage as described above for link 202B.

Imaging of the implantation site, and positioning of spacer 200 in any of the embodiments shown and described herein, may be carried out in a manner understood within the art, for example using a C-arm fluoroscope, to ensure proper placement of embodiments of the disclosure. For example, any element shown in FIG. 9 may be radiographic, for example radiopaque. Alternatively, only some elements may be radiographic, for example to facilitate an understanding of an orientation of spacer 200 within the body. In one embodiment, one or more radiographic pins 248, for example three pins for revealing a three dimensional disposition, or other elements are added to spacer 200, for example to pin 202B in FIG. 9, to facilitate visualization under imaging, particularly as spacer 200 is progressively moved across the disc space and into a final position within the body.

One or more projections 262, sized and dimensioned to engage body tissue and secure link 202B in a desired location, are provided extending from one or both of an upper and lower surface, 264, 266, respectively, of link 202B. Projections 262 may have the form of pyramidal shaped teeth, for example. Additional apertures 268 may be provided within a body of link 202/202B to permit the insertion of radiopaque elements, to connect to surgical tools, or to promote bone ingrowth into link 202/202B, or through link 202/202B between adjacent bones.

Figure 16:
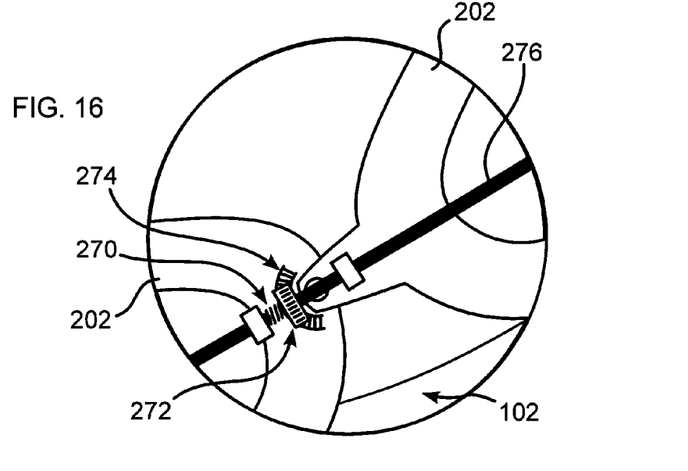
FIG. 16 depicts an enlarged view of a portion of the spacer of FIG. 2, depicting a gear mechanism for changing a relative angle of successive links in accordance with the disclosure.

Referring now to FIG. 16, a system of gears and drive shafts cooperate to allow precise control over an extent of curling of respective links 200 of the disclosure. In the embodiment shown, flex connector 270, for example a spring or resilient material, transfers rotational movement between successive links 202. Additionally, gear 272 engages a rack 274 upon a surface of a link 202, to rotate adjacent links relative to each other. A length of rack 274 determines a range of angular displacement of the adjacent links 202. Successive links so joined in this manner all change relative angles as shaft 276 is rotated. Shaft 276 extends outside the body, or may be connected to an extension outside the body, so an angle may be changed during and after spacer 200 implantation, for example during imaging. It should be understood that many different alternative combinations of gears and shafts may be provided to achieve the same or a similar result, as would be understood within the art, and this is but one such example.

A spacer 200 in accordance with the instant disclosure may be inserted using an MIS approach (a reduced incision size, with fewer and shorter cuts through body tissue), and may be implanted through a small tubular instrument, reducing time under anesthesia and reducing trauma to the patient. By positioning numerous links 202 within the intervertebral space, and particularly if the links 202 are positioned between sturdy tissue, for example along the cortical rim, a potential for harmful subsidence of adjacent vertebrae 102 is reduced. In addition, by enabling various sized shaped links 202, a spacer 200 of a desired size may be formed, and a spacer 200 may be formed with a specific shape and size at desired locations along its length, for optimal placement within the body.

Devices of the disclosure additionally permit an advantageous posterior approach to the spine, simplifying surgery, and reducing risk and trauma to the patient. For example, spacer 200 may be implanted in a transforaminal approach. In addition, they may advantageously be used in combination with other known or hereinafter developed forms of fixation. Spacer 200 and other devices of the disclosure are advantageously fabricated from biocompatible materials, including any combinations of PEEK (polyether ether ketone), titanium (advantageously of sufficient purity for use in the body) and alloys thereof, and or tantalum. There are many other biocompatible materials which may be used, including other plastics and metals, as well as fabrication using living or preserved tissue, including autograft, allograft, and xenograft material, each selected according to a required strength, durability, and other characteristics. Materials may be combined with therapeutic substances, including agents for promoting healing, anti-microbial growth, or bone growth. Materials may also be formed with biodegrading materials, particularly, for example, where bone ingrowth and fusion is expected.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An intervertebral spacer for therapeutic treatment of a patient, comprising:
    at least one link having a body with a first opening extending from an upper surface to a lower surface sized and dimensioned to fit within an intervertebral space in the patient and configured to maintain a separation of two adjacent vertebrae for a period of time;
    at least one rigid guiding object insertable into the patient, said at least one rigid guiding object and said at least one link sized to be insertable into the patient using an MIS approach;
    at least one pivot connected between an end of one of said at least one link and an end of one of said at least one rigid guiding object, said at least one pivot configured to limit a relative range of angular orientation of said one of said at least one link and said one of said at least one rigid guiding object, said at least one pivot configured to transfer an insertion force from said at least one rigid guiding object to said at least one link, to advance said at least one link into the intervertebral space,
    a pivoting joint connected between adjacent links, and
    a resilient catch, the resilient catch being configured to couple to a hook element provided in an adjacent link having a body with a second opening therethrough, wherein the body with the first opening therethrough does not contact the body with the second opening therethrough when the resilient catch is coupled to the hook element,
    wherein the upper surface of the body is configured to contact one of the two adjacent vertebrae and the lower surface of the body is configured to contact the other of the two adjacent vertebrae,
    wherein the resilient catch bends to allow insertion of the hook element,
    wherein the resilient catch and hook element are provided between the same adjacent links as the pivoting joint.

2. The spacer of claim 1, further comprising:
    a tube for receiving the spacer extendable from outside of the patient's body into the patient's body.

3. The spacer of claim 2, further including
    a flexible line through an aperture formed in a leading end of at least one of said at least one link, said leading end defined as the end first advanced into the intervertebral space, said line passable from outside of the patient's body, through said aperture, and back outside the patient's body, said line having sufficient strength to guide said leading end by exerting a force upon said leading end when said at least one link is advanced into the intervertebral space.

4. The spacer of claim 1, wherein said at least one link includes at least three links, said at least three links insertable into the body in a first relative substantially aligned orientation relative to each other, and formable into a curved alignment in the intervertebral space, each link positionable at least in part over cortical bone in the intervertebral space.

5. The spacer of claim 1, further including an elongated guiding member configured to pass into the body and push said at least one link into the intervertebral space.

6. The spacer of claim 1, further including an elongated guiding member configured to extend from outside of the patient's body into the patient's body, and to push said at least one link within the intervertebral space.

7. The spacer of claim 1, wherein the at least one link includes a curved surface opposite a flat surface.

8. The spacer of claim 1, wherein the pivoting joint includes
    a flexible connector extending between and connected to adjacent ones of said at least one link; and
    a latch mechanism operative to maintain an angular displacement between said adjacent ones of said at least one link when said adjacent ones of said at least one link are pivoted to a predetermined angle relative to each other.

9. The spacer of claim 8, comprising at least five links, wherein one of the links is larger than the other links.

10. The spacer of claim 1, further including a stop projection adjacent at least one of said pivoting joint, said stop configured to limit an extent of angular displacement between adjacent ones of said at least one link.

11. The spacer of claim 1, at least one of said at least one link including one or more apertures through which bone of the patient may grow.

12. The spacer of claim 1, at least one of said at least one link including a therapeutic substance operative to promote at least one of healing, anti-microbial growth, and bone growth.

13. The spacer of claim 1, wherein there are at least two of said at least one link, and said at least two links have a substantially different shape.

14. The spacer of claim 1, further including a tapered edge formed along at least one end of at least one of said at least one link.

15. The spacer of claim 1, further including an aperture formed in at least one end of at least one of said at least one link, said aperture sized to admit passage of a flexible line passable through said aperture when said link is within the intervertebral space to extend outside of the patient, whereby a force exerted upon said line is operative thereby to change a position of said spacer within the intervertebral space.

16. The spacer of claim 1, wherein said at least one guiding object is a successive one of said at least one link.

17. The spacer of claim 1, wherein the pivoting joint includes a connecting member and at least one pin, wherein the at least one pin pivotally connects the connecting member to the at least one link.

18. The spacer of claim 1, wherein the pivoting joint includes a connecting member, a first pin, and a second pin, wherein the first pin pivotally connects a first end of the connecting member to one of the at least one link and the second pin pivotally connects a second end of the connecting member to the adjacent link.

19. An intervertebral spacer for therapeutic treatment of a patient, comprising:
- a plurality of flexibly connected links sized and dimensioned to fit within an intervertebral space in the patient and configured to maintain a separation of two adjacent vertebrae for a period of time, said links insertable into the patient through a tube using a reduced size MIS incision, each of said links comprising a body with an enclosed perimeter; and
- a plurality of pivots each forming said flexible connection between adjacent ones of said plurality of links, said plurality of pivots configured to limit a relative range of motion of adjacent links relative to each other, said plurality of pivots cooperative to form said plurality of links into a radiused configuration corresponding to cortical bone within an intervertebral space of the patient, and
- a resilient catch, the resilient catch being configured to couple to a hook element provided in an adjacent link, wherein the resilient catch bends to allow insertion of the hook element, wherein the resilient catch and hook element are provided between the same adjacent links as at least one of the plurality of pivots.

20. The spacer of claim 19, said plurality of pivots configured to form a chain of said plurality of links having a leading link and a trailing link, the trailing link pushable to advance said chain into the vertebral space, said leading link pullable to guide said chain into a curved configuration corresponding to the patient's intervertebral space.

* * * * *